US00PP25044P3

(12) United States Plant Patent
Hamilton et al.

(10) Patent No.: US PP25,044 P3
(45) Date of Patent: Nov. 11, 2014

(54) RASPBERRY PLANT NAMED 'DRISRASPSIX'

(50) Latin Name: ***Rubus idaeus* L.**
Varietal Denomination: DrisRaspSix

(75) Inventors: Brian K. Hamilton, Richmond, TX (US); Carlos D. Fear, West Malling (GB); Richard E. Harrison, Aptos, CA (US); Miguel H. Ahumada, Ojai, CA (US); Matthias Vitten, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 216 days.

(21) Appl. No.: 13/507,990

(22) Filed: Aug. 10, 2012

(65) Prior Publication Data

US 2014/0047596 P1 Feb. 13, 2014

(51) Int. Cl.
*A01H 5/00* (2006.01)

(52) U.S. Cl.
USPC ..... Plt./204

(58) Field of Classification Search
CPC ..... A01H 5/0887; A01H 5/08; A01H 5/0831; A01H 5/00; A01H 5/0216
USPC ..... Plt./204, 201
See application file for complete search history.

*Primary Examiner* — June Hwu
(74) *Attorney, Agent, or Firm* — Jondle Plant Sciences Divison of Swanson & Bratschun, L.L.C.

(57) ABSTRACT

A new and distinct variety of raspberry plant named 'DrisRaspSix' particularly distinguished by having high productivity, partially self-fruitful plants bearing medium sized, bright red berries, is disclosed.

2 Drawing Sheets

Genus and species: *Rubus idaeus* L.
Variety denomination: 'DrisRaspSix'.

BACKGROUND OF THE NEW PLANT

The present invention relates to a new and distinct raspberry variety designated 'DrisRaspSix' and botanically known as *Rubus idaeus* L. This new raspberry variety was discovered in Ventura, Calif. in February 2004 and originated from a cross between the proprietary female parent raspberry plant 'Driscoll Maravilla' (U.S. Plant Pat. No. 14,804) and the proprietary male parent raspberry plant 'Driscoll Francesca' (U.S. Plant Pat. No. 14,860). The original seedling of the new variety was first asexually propagated at a nursery in Santa Cruz, Calif. 'DrisRaspSix' was subsequently asexually propagated and underwent further testing at a nursery in Ventura, Calif. for nine years. The present invention has been found to be stable and reproduce true to type through successive asexual propagations via tissue culture and root cuttings.

Plant Breeder's Rights for this variety have not been applied for. 'DrisRaspSix' has not been made publicly available or sold more than one year prior to the filing date of this application.

SUMMARY OF THE INVENTION

The following are the most outstanding and distinguishing characteristics of this new variety when grown under normal horticultural practices in Ventura, Calif.:

1. High productivity;
2. Partially self-fruitful plant; and
3. Medium sized, bright red berries.

DESCRIPTION OF THE PHOTOGRAPHS

This new raspberry plant is illustrated by the accompanying photographs which show fruit of the plant as well as the primocanes. The colors shown are as true as can be reasonably obtained by conventional photographic procedures. The photographs are of plants that are six months old.

DESCRIPTION OF THE NEW VARIETY

Figure 1:
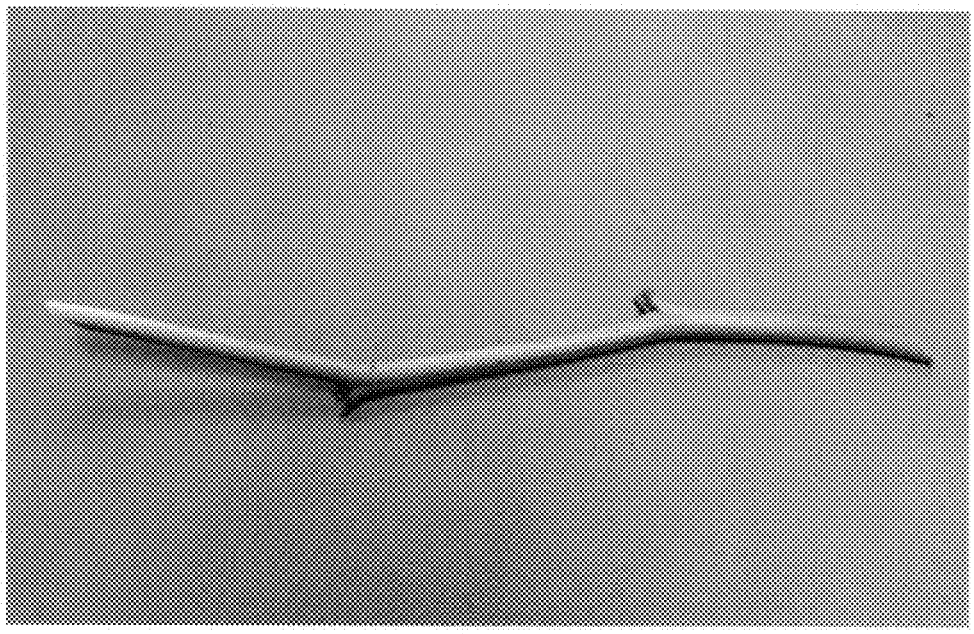
FIG. 1 shows a section of a young cane with prickles.
Figure 2:
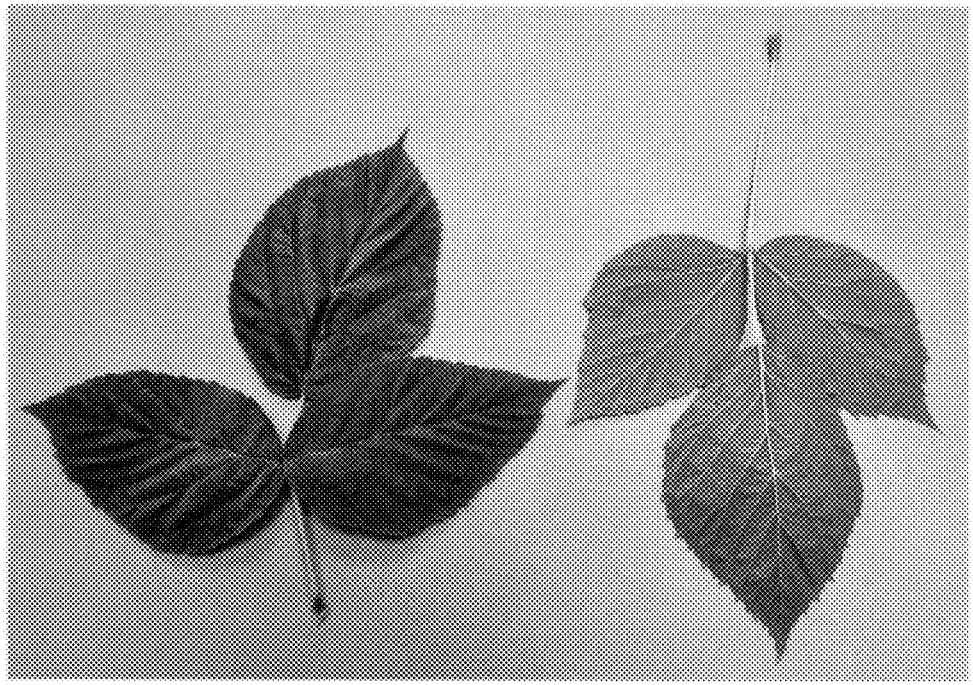
FIG. 2 shows both the upper surface and the lower surface of the plant leaves.
Figure 3:
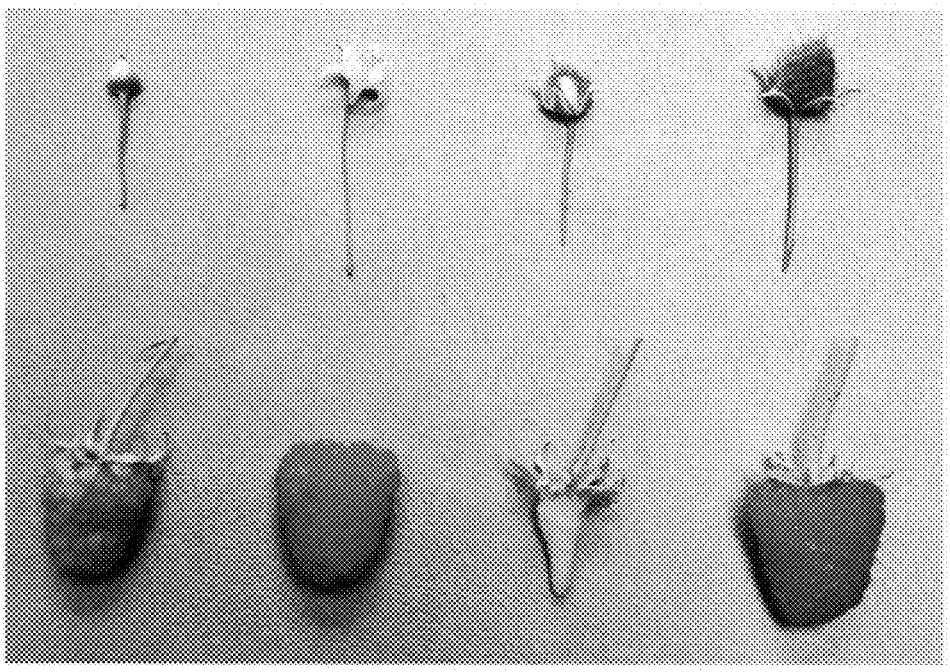
FIG. 3 shows close-up views of typical flowers and fruit at various stages of development.

The following detailed descriptions set forth the distinctive characteristics of 'DrisRaspSix'. The data which define these characteristics is based on observations taken in Ventura, Calif. from 2003 to 2011. This description is in accordance with UPOV terminology. Color designations, color descriptions, and other phenotypical descriptions may deviate from the stated values and descriptions depending upon variation in environmental, seasonal, climatic and cultural conditions. 'DrisRaspSix' has not been observed under all possible environmental conditions. The botanical description of 'DrisRaspSix' was taken from six-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family.*—Rosaceae.
*Botanical.*—*Rubus idaeus* L.
*Common name.*—Raspberry.
*Variety name.*—'DrisRaspSix'.

Parentage:

*Female parent.*—The proprietary raspberry plant 'Driscoll Maravilla' (U.S. Plant Pat. No. 14,804).

*Male parent.*—The proprietary raspberry plant 'Driscoll Francesca' (U.S. Plant Pat. No. 14,860).

Plant:

*Propagation.*—Tissue culture and root cuttings.

*Size.*—Medium.

*Height.*—21.5 cm.

*Width.*—17.5 cm.

*Length/width ratio.*—1.2.

*Productivity.*—High.

*Self-fruitfulness.*—Partially self-fruitful.

*New cane growth habit.*—Semi-erect.

Primocanes:

*Number of canes.*—Medium; 9.6.

*Glaucosity (waxy bloom) on full grown shoot after picking.*—Medium.

*Cane length in autumn.*—Medium.

*Cane length for current season's cane in autumn.*—18.13 cm.

*Length of internode.*—Very long.

*Internodal distance at central ⅓ of cane.*—9.83 cm.

*Length of vegetative bud.*—Long.

*Number of young shoots.*—Medium; 12.4.

*Primocane color.*—RHS 144B.

*Anthocyanin coloration of apex during rapid growth.*—Present.

*Intensity of anthocyanin coloration of apex during rapid growth.*—Weak.

*Time of young shoot emergence from the soil.*—Medium; January.

*Time of beginning of flowers.*—Medium; May.

*Time of beginning of fruit ripening in autumn.*—Medium; 1st week of June.

*Length of fruiting period in autumn.*—Medium; June through 1st week of October.

*Percent of cane flowering as primocane.*—35%.

*Percent primocane yield of total yield.*—50%.

*Glaucosity (waxy bloom) on current years cane in autumn.*—Medium.

*Cane strength.*—Medium.

*Shape of cane cross section.*—Rounded to angular.

*Pubescence on canes.*—Absent.

Floricanes:

*Dormant cane length in summer.*—Medium (Pruned).

*Dormant cane color in summer.*—RHS N200D (Light brown).

*Fruiting lateral attitude.*—Semi-erect.

*Time of vegetative bud burst.*—Medium; last week of February.

*Time of beginning of flowers.*—Medium; 3rd week of March.

*Time of beginning of fruit ripening.*—Medium; 1st week of April.

*Length of fruiting period.*—Medium; 1st week of May through 1st week of July.

Prickles (spines):

*Density of spines on central third.*—Sparse.

*Size of base of prickles.*—Small.

*Length (from base to tip).*—Very short.

*Length at 1.0 m height at end of harvest season (from base to tip).*—1.22 mm.

*Color (pigmentation).*—RHS 125A (Green) and 60A (Red-purple).

*Attitude of tip.*—Horizontal to downward.

*Size.*—Very small.

*Texture.*—Soft.

*Presence and distribution on petioles.*—Present and irregularly distributed.

Leaves:

*Terminal leaflet.*—Length: Medium; 9.98 cm. Width: Medium; 6.59 cm. Length/width ratio: 1.5. Leaf color: Upper surface: RHS 137A (Dark green). Lower surface: RHS N138D (Medium green). Profile in cross section: Flat (straight). Relief between the veins: Medium. Overlapping of leaflets: Overlapping. Glossiness: Medium. Shape: Ovate. Apex: Truncate. Base: Obtuse. Margin: Crenate. Arrangement: Simple.

*Lateral leaflets (basal pair).*—Number of leaflets: Usually 3. Size: Length: 9.02 cm. Width: 5.58 cm. Length/width ratio: 1.6. Arrangement: Compound-opposite (2 leaves per node). Shape: Ovate. Apex: Truncate. Base: Obtuse. Margin: Crenate. Lateral leaflet (length to stalklet, lower pair): Short. Rachis length between terminal leaflet and adjacent lateral leaflets.—19.3 mm.

Stipules:

*Orientation.*—Erect.

Flowers:

*Size.*—Small.

*Diameter.*—10.71 mm.

*Petal length.*—6.39 mm.

*Petal width.*—2.92 mm.

*Length/width ratio.*—2.2.

*Petal color.*—RHS 157C.

*Flower bud.*—Color: RHS 143C. Length: 13.6 mm. Width: 8.76 mm.

*Flowering period.*—Primocane: Medium; Early June to mid-September. Floricane: Medium; Late March to late June.

*Pedicel.*—Number of spines: Absent or very few. Anthocyanin coloration: Absent. Color: RHS 143C. Length: Short; 20.33 mm. Diameter: 1.05 mm.

*Sepal.*—Color: RHS 143C. Length: 12.6 mm. Width: 6.54 mm.

Peduncle:

*Presence of anthocyanin coloration.*—Absent.

*Intensity of anthocyanin coloration.*—Absent.

*Color.*—RHS 143C.

Fruit:

*Length.*—Medium; 23.56 mm.

*Width.*—Medium; 20.65 mm.

*Ratio of length to width.*—1.1; As long as broad.

*Average number of drupelets per fruit.*—51.

*Weight (g/fruit).*—Primocane: 6.5. Floricane: 6.0.

*Soluble solids (% in Brix).*—10.5.

*Weight of seeds (g/seed).*—0.001469.

*Size.*—Medium.

*Shape.*—Ovate (broad conical).

*Size of single drupelet.*—Medium.

*Color.*—Immature fruit: RHS 145B (Light yellow-green). Maturing fruit: RHS 33C (Light orange-red). Mature fruit color: RHS 53A (Dark red).

*Glossiness.*—Medium.

*Firmness.*—Medium.

*Adherence to plug.*—Medium.

*Main bearing type.*—Both on previous years cane in summer and on current years cane in autumn.

*Time of ripening.*—Primocane: Medium; 1st week of June. Floricane: Medium; 2nd week of May.

*Harvest season.*—Primocane: Mid-July to early October. Floricane: Mid-May to late July.

*Yield.*—High.

Pest resistance: *Tetranychus urticae*: Susceptible.

COMPARISON WITH PARENTAL AND COMMERCIAL VARIETIES

'DrisRaspSix' differs from the proprietary female parent 'Driscoll Maravilla' (U.S. Plant Pat. No. 14,804) in that 'DrisRaspSix' has a medium plant size, medium glaucosity on primocanes, and medium time of cane emergence, whereas 'Driscoll Maravilla' has a large plant size, weak glaucosity on primocanes, and late time of cane emergence. Additionally, 'DrisRaspSix' has medium size fruit and is partially self-fruitful, whereas 'Driscoll Maravilla' has large size fruit and is self-fruitful.

'DrisRaspSix' differs from the proprietary male parent 'Driscoll Francesca' (U.S. Plant Pat. No. 14,860) in that 'DrisRaspSix' has terminal leaflets with an obtuse base and a crenate margin, whereas 'Driscoll Francesca' has terminal leaflets with a cordate base and a doubly serrate margin. Additionally, 'DrisRaspSix' has fruit with medium glossiness and is partially self-fruitful, whereas 'Driscoll Francesca' has fruit with weak glossiness and is self-fruitful.

'DrisRaspSix' differs from commercial variety 'DrisRaspThree' (U.S. Plant Pat. No. 23,477) in that 'DrisRaspSix' has a medium sized plant having a semi-erect new cane growth habit, whereas 'DrisRaspThree' has a large sized plant having an erect or upright new cane growth habit. In addition, 'DrisRaspSix' has medium sized fruit with an average of 51 druplets per fruit, whereas 'DrisRaspThree' has medium to large sized fruit with an average of 76 druplets per fruit.

We claim:

1. A new and distinct variety of raspberry plant named 'DrisRaspSix' as described and shown herein.

* * * * *